United States Patent [19]

Pierce

[11] Patent Number: 4,648,861
[45] Date of Patent: Mar. 10, 1987

[54] FOLDING APPARATUS AND METHOD
[75] Inventor: Allan A. Pierce, Outagamie County, Wis.
[73] Assignee: Kimberly-Clark Corporation, Neenah, Wis.
[21] Appl. No.: 748,658
[22] Filed: Jun. 25, 1985
[51] Int. Cl.[4] ............................................. B65H 45/30
[52] U.S. Cl. .................... 493/333; 493/394; 493/418; 493/422
[58] Field of Search ............... 493/418, 422, 458, 450, 493/451, 938, 960, 333, 394

[56] References Cited

U.S. PATENT DOCUMENTS

| | | | |
|---|---|---|---|
| 2,031,687 | 2/1936 | Boriski | 223/37 |
| 2,853,215 | 9/1958 | Steele | 223/37 |
| 3,552,736 | 1/1971 | Frick et al. | 493/331 |
| 3,685,818 | 8/1972 | Burger et al. | 493/418 |
| 3,782,714 | 1/1974 | Spencer et al. | 493/250 |
| 4,067,336 | 1/1978 | Johnson | 604/389 |
| 4,133,252 | 1/1979 | Eckstein et al. | 493/341 |
| 4,200,032 | 4/1980 | Roda | 493/451 |
| 4,285,686 | 8/1981 | Ambler | 493/439 |

Primary Examiner—Frederick R. Schmidt
Assistant Examiner—William E. Terrell
Attorney, Agent, or Firm—P. A. Leipold; D. L. Traut; J. J. Duggan

[57] ABSTRACT

The present invention involves a folding apparatus for folding a flexible sheet during the manufacture of an article such as a diaper or personal incontinence pad. Briefly, the apparatus comprises at least one folding board. The folding board, in turn, comprises four panels which are joined by three hinges for allowing the board to bend along three specified fold lines. The first hinge allows the board to bend between the first and second panel along a first centrally-located fold line which extends from the leading edge of the folding board to the trailing edge. The second hinge allows the board to bend between the first and third panel along a second fold line which extends from the leading edge to one of the sides edges of the board. The third hinge allows the board to bend between the second and fourth panel along a third fold line which extends from the leading edge to the other side edge of the board. The apparatus also provides for bending the board along these fold lines as well as for releasably retaining a flexible sheet on the board during the folding operation.

13 Claims, 7 Drawing Figures

FOLDING APPARATUS AND METHOD

BACKGROUND OF THE INVENTION

The prior art is replete with structures relating to perineal protective devices including such items as garment shields, drip containment or dribble cups, sanitary napkins, diapers, incontinent pads and the like. Such devices range from very thin material for protecting against garment stains which might otherwise result from small amounts of involuntary fluid discharge, to pads having sufficient capacity to absorb the full flow of menstrual fluid discharge, to still heavier pads for infant diapering and for collecting, absorbing and retaining the entire discharge of adult incontinence.

Particular shapes have been devised in an attempt to obtain good body conformance, leakage prevention, and comfort. While many are designed for re-use and are made from launderable fabrics, the most recent developments have been directed to disposable materials including non-woven webs, thin plastic films, and thick pads of absorbent fibers, in particular air-formed pads of wood cellulose fibers. A major difficulty with most of the disposable materials is that they do not have the drapability of more permanent cloth-like material and therefore will not conform well to the body, especially when made thick enough to provide the absorbent capacity needed for catamenial and diapering uses.

Various attempts have been made to obtain conformity by selecting particular geometries. While many of these obtain a good fit when first applied, they do not have the ability to move with changing body configurations. As a result, the material located between the thighs is often crushed by leg pressure soon after application, and thereby loses its initial conformance, resulting in gaps between the protective device and the body, or causing discomfort because of rubbing and/or chafing contact between the device and the body.

U.S. Pat. No. 4,067,336, to Russell L. Johnson, and assigned to the same assignee as the present invention, discloses a perineal protective device made from flexible sheet material which when folded on a set of pre-established lines assumes a self-adjusting, body-conforming shape, achieving improved comfort and containment characteristics while being well-suited for all size devices ranging from the above-mentioned relatively thin garment protectors to absorbent pads which handle full-discharge incontinents.

The protective device disclosed by Johnson comprises a sheet of flexible material of generally rectangular form adapted for folding on a set of pre-established fold lines. The sheet material is generally defined by a top body-contacting surface, a bottom surface, a front edge, a back edge, and two side edges. The pre-established fold lines along which the sheet material is folded prior to use comprise: (a) a main fold line centrally and longitudinally disposed along the major axis of the sheet and extending the full length of the sheet; (b) a first pair of rearwardly directed diverging fold lines originating on the main fold line from a common base point spaced inwardly from the front edge of the sheet, and extending to the sheet perimeter; and (c) a second pair of rearwardly directed diverging fold lines disposed between the first pair of diverging lines and the side edges of the sheet, with the second pair of lines also originating at the same common base point on the main fold line as the first set of lines and extending to the sheet perimeter.

The sheet material is adapted for inward folding on the main fold line, outward folding on the first pair of rearwardly diverging lines, and inward folding on the second pair of rearwardly diverging lines. When folded in this way, the sheet material has an upwardly concave or bent configuration in both the transverse and longitudinal directions. The deepest part or the greatest depth of the concavity in both directions originates at the common base point on the main fold line.

Johnson teaches that the manufacturer may either prefold the sheet material or simply prepare it for folding by the consumer just prior to use. Experience has shown that, in the interest of consumer convenience, it is preferable for the manufacturer to fold the device. Unfortunately, this specific fold has proven to be relatively difficult to perform in large scale production. In particular, because this fold is nonsymmetrical about its lateral axis, and because the material of the pad can be relatively thick, conventional automated folding apparatus have been unsatisfactory. Likewise, manual folding is undesirable because of the need for sterility and the higher costs involved.

In the interest of cost efficiency, disposable articles such as these are typically produced on a fully automated assembly line which necessarily moves at high speeds. It is thus desirable for the folding process to likewise be fully automated and also to be performed at rates at least as high as the rest of the assembly line.

SUMMARY OF THE INVENTION

The present invention involves a folding apparatus for folding a flexible sheet during the manufacture of an article such as a diaper or personal incontinence pad. Briefly, the apparatus comprises at least one folding board. The folding board in turn comprises four panels which are joined by three hinge means for allowing the board to bend along three specified fold lines. The first hinge means allows the board to bend between the first and second panel along a first centrally located fold line which extends from the leading edge of the folding board to the trailing edge. The second hinge means allows the board to bend between the first and third panel along a second fold line which extends from the leading edge to one of the side edges of the board. The third hinge means allows the board to bend between the second and fourth panel along a third fold line which extends from the leading edge to the other side edge of the board. The apparatus also comprises means for bending the board along these fold lines as well as means for releasably retaining a flexible sheet on the board during the folding operation.

In accord with a preferred embodiment of the present invention, the folding apparatus comprises a plurality of folding boards as described above. The folding boards are mounted on an endless chain which repeatedly brings each board into contact with the source of sheets to be folded. After a sheet is placed on a folding board, the board is made to bend along the fold lines, thereby folding the sheet, as it travels toward the point where the folded sheet is removed. The board then cycles back to the point where it can pick up another sheet to fold. In this embodiment, the sheets are held in place by means of vacuum ports on the folding boards connected to a vacuum source which is temporarily interrupted when the sheets are ready to be removed from the boards.

BRIEF DESCRIPTION OF THE DRAWINGS

The invention will be more fully described in conjunction with the following drawings wherein.

DETAILED DESCRIPTION

Figure 1:
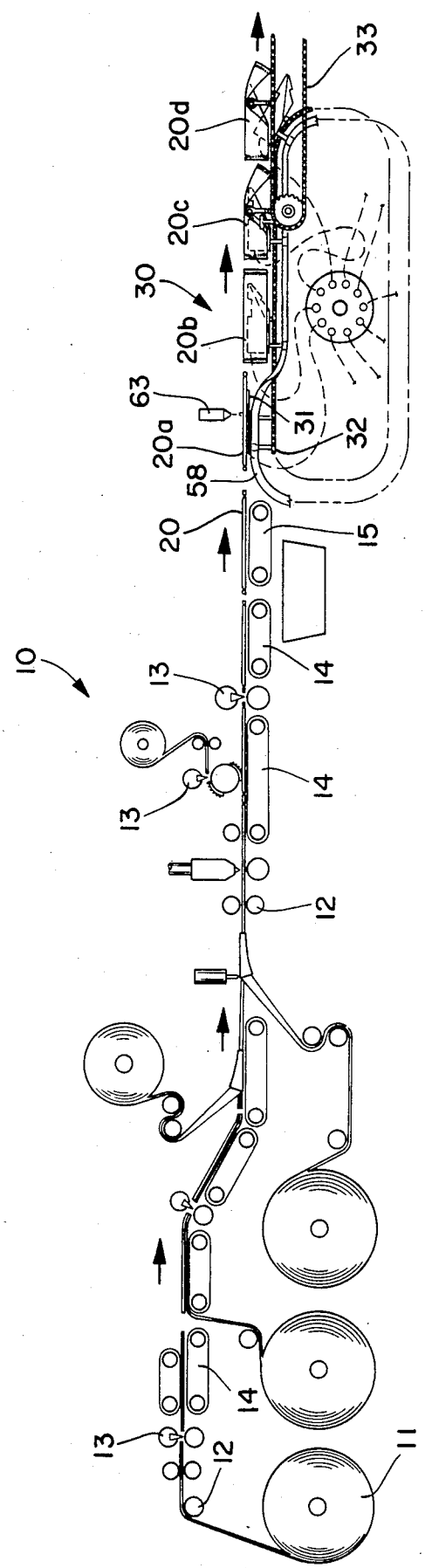
FIG. 1 is a side elevation of an automated assembly line for producing disposable incontinence pads and which includes the folding apparatus of the present invention.

Referring to the drawings, FIG. 1 shows a completely automated assembly line 10 for production of disposable waste containment garments 20d, in this case adult size personal incontinence pads. The assembly line moves generally in the direction indicated by the arrows. Through a series of rollers 12, conveyors 14, and cutters 13, the unfolded sheet 20 is assembled from the starting materials on rolls 11. The conveyor 15 brings the unfolded sheet 20 into position to be picked up by the folding apparatus 30 which is made in accordance with the present invention. In particular, the unfolded sheet 20 is held one of the folding boards 31 which is moving on the endless chain 32. After folding, the garment 20d is removed from the folding board and taken by another endless chain 33 to a stacking apparatus and/or packaging apparatus (not shown).

Figure 2:
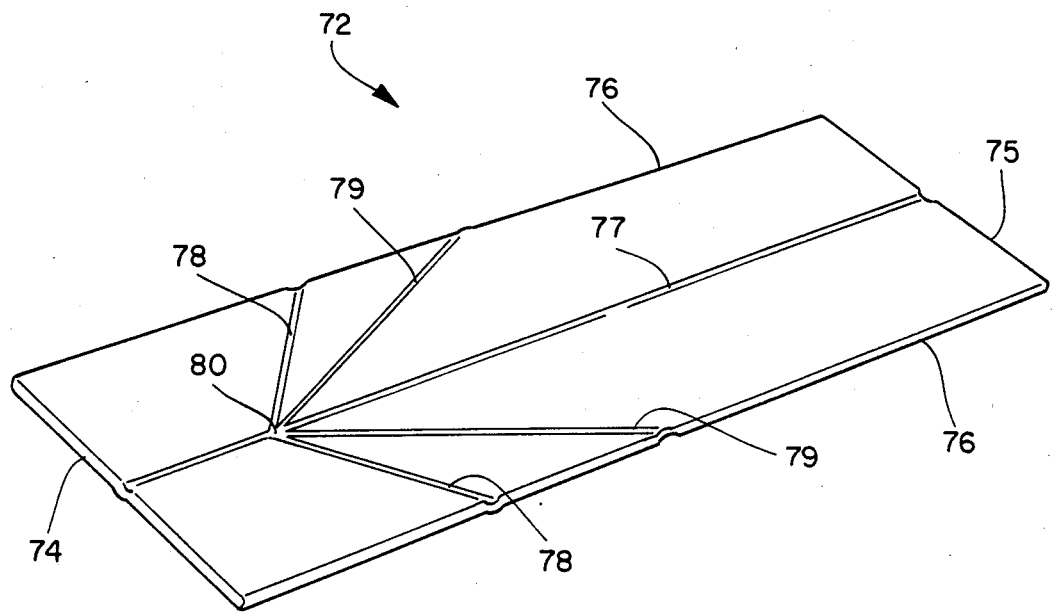
FIG. 2 is a top perspective view of a rectangular flexible sheet showing the arrangement of the fold lines used to form the incontinence pad of FIG. 3.

FIG. 2 depicts an example of the unfolded garment 72 which can be folded along the indicated fold lines with the folding apparatus of the present invention. This garment is the subject of U.S. Pat. No. 4,067,336, the entire disclosure of which is incorporated herein by reference. Generally, the sheet is elongate and rectangular, thus having a front edge 74, a back edge 75 and two side edges 76. Preferably, the sheet comprises different layers of materials, such as an outer water impermeable layer and a water absorbent layer.

The lines on which the sheet will be folded include a main fold line 77 centrally and longitudinally disposed along the major axis; a first pair of rearwardly diverging fold lines 78 originating on main fold line 77 from a common base point 80 spaced inwardly from the front edge 74 and extending to the sheet perimeter at side edges 76; and a second pair of rearwardly diverging fold lines 79 also originating from base point 80 and disposed in spaced arrangement between the first pair of diverging lines 78 and side edges 76 and terminating at side edges 76.

Figure 3:
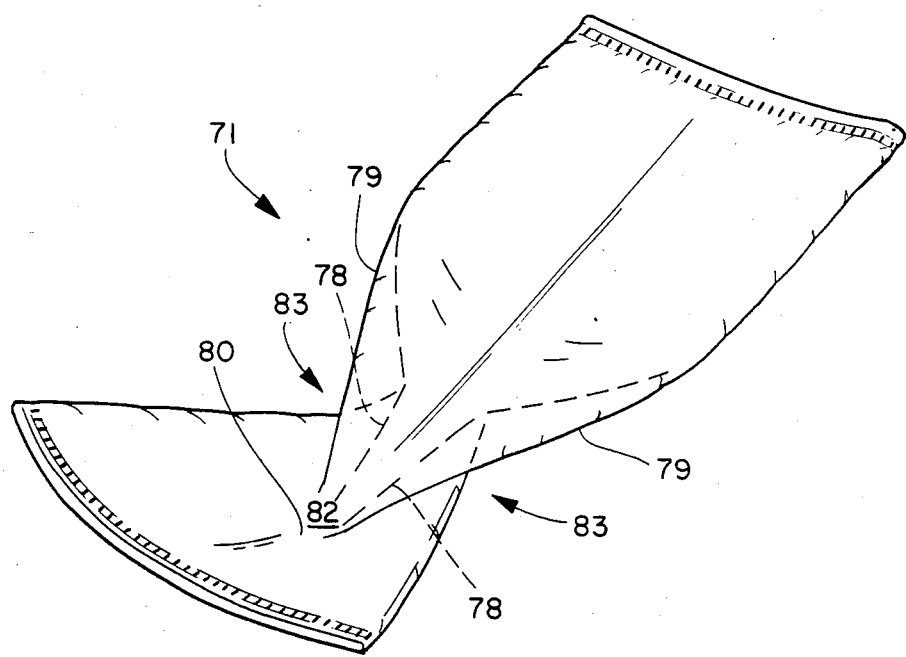
FIG. 3 is a perspective view of a folded personal incontinence pad which can be folded with the apparatus of the present invention.

FIG. 3 is a perspective view of the garment 71 after it has been folded along the above described fold lines. As can be seen, the folds have produced a cup 82 towards the front of the garment 71. The deepest point in the cup 82 is the common base point 80 for the pairs of rearwardly diverging fold lines 78 and 79. In addition, the folds have resulted in a narrow portion 83 which is adapted to comfortably fit between the legs of the wearer.

Figure 4:
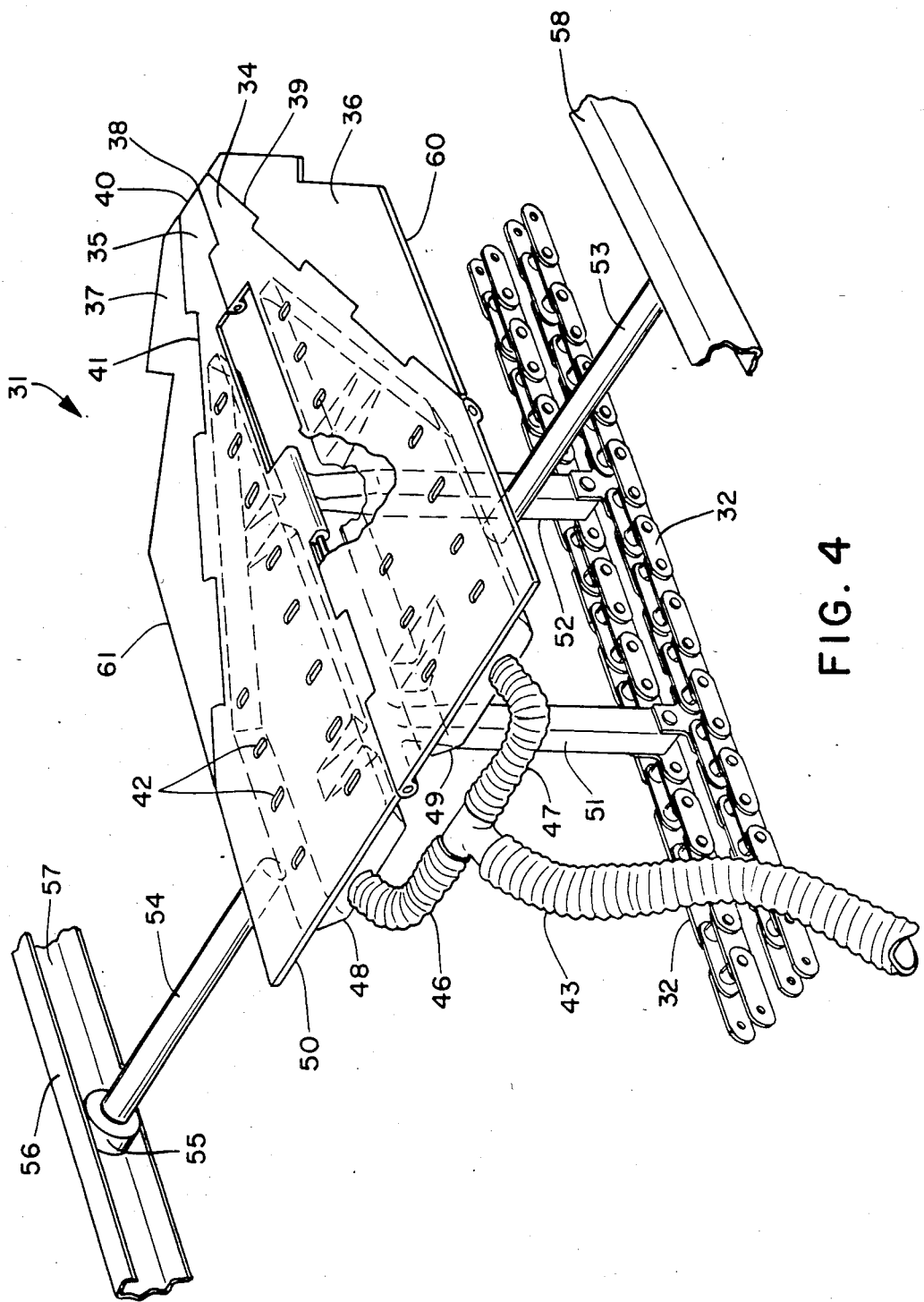
FIG. 4 is a top perspective view of a folding board in acordance with the present invention.

FIG. 4 shows a folding board 31 made according to the preferred embodiment of the present invention. The board 31 comprises a first interior panel 34 and second interior panel 35 both of which are joined at hinge 38. A third panel 36 is joined to the first panel 34 at hinge 39. Similarly, a fourth panel 37 is joined to the second panel 35 at hinge 41.

As can be seen, the hinge 38 runs centrally from the front 40 to the back 50 of the board 31, thus allowing the board 31 to bend along a first longitudinal fold line. Also, the hinge 39 runs between the front 40 and the side 60 of the board 31, thus allow the board 31 to fold along a second fold line which is at an acute angle to the first fold line. Likewise, the hinge 41 runs between the front 40 and the side 61, thus allowing the board to bend along a third fold line which is at a similar acute angle to the first fold line. For purposes of symmetry, the the second panel is preferably a mirror image of the first panel. Likewise, the fourth panel is preferably a mirror image of the third panel.

The first and second panels 34 and 35 of the folding board 31 also includes a series of vacuum ports 42 on their upper surface. The purpose of these ports 42 is to retain the garment on the board during the folding process. As depicted by the hidden lines, the ports 42 communicate with a first and second hollow chamber 48 and 49 which lie under the top surface of the folding board. The chambers 48 and 49 communicate with vacuum hoses 46 and 47 respectively, which in turn communicate with the vacuum hose 43 which communicates with a vacuum source (see FIG. 5).

The folding board 31 is supported by posts 51 and 52 which are mounted on the chains 32. Also, a tracking rod 54 is attached to the second panel 35. A roller 55 is located at the end of the rod 54 and is adapted to roll within the track 57 of the guide 56. Likewise, a tracking rod 53 is attached to the first panel 34 which has a roller (not shown) which rolls in the track of the guide 58.

Preferably, the folding board also includes a pair of springs (not shown) which are connected between the first and third panels and the second and fourth panels respectively and which operate to keep the folding board flat at these second and third fold lines. Alternatively, rods can be attached to the third and fourth panels, which rods could ride in a separate pair of tracks and thereby cause the third and fourth panels to flatten.

Figure 5:
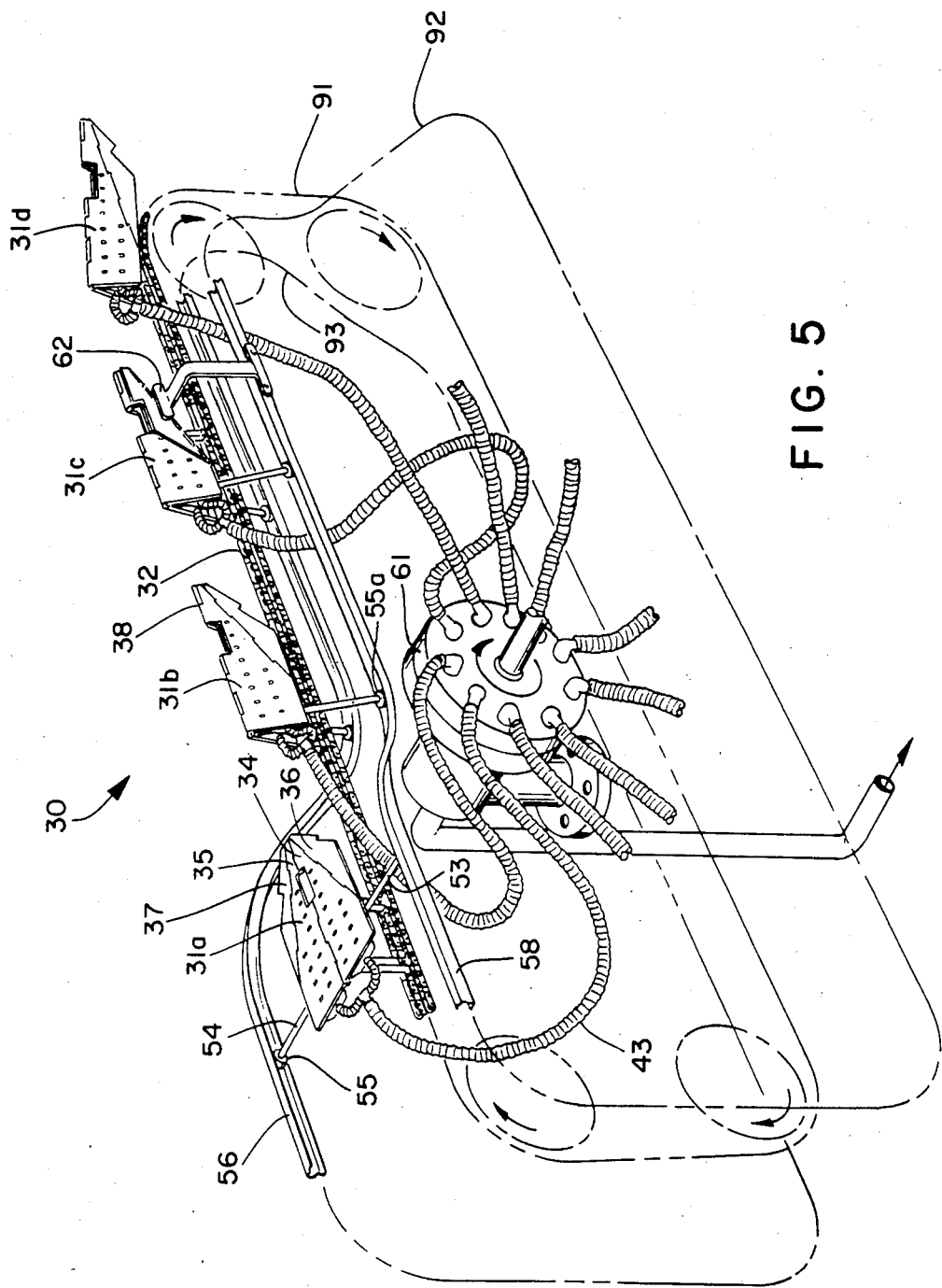
FIG. 5 is a perspective view of a folding apparatus in accordance with the present invention particularly showing the sequential bending of the folding boards.

FIG. 5 shows a folding apparatus 30 made according to the present invention wherein a plurality of folding boards 31a–31d are mounted on the endless chain 32. Preferably, there would be about 10 folding boards on the chain 32. However, for the sake of convenience and understanding, the folding boards located on the side and bottom portions of the chain 32 have not been illustrated.

The apparatus 30 includes a rotating drum 61 to which the vacuum hoses 43 are attached. The drum 61 communicates with a vacuum source. As can be seen, the vacuum hoses 43 are preferably flexible.

The folding board 31a is in the flat or unfolded position. This is the condition which is need for the folding boards before they receive a sheet to fold. This flat condition is achieved because the rollers 55 and 55a are in the track 56 and 58, and the tracks are high enough above the chain 32 and far enough apart so that the rods 53 and 54 are caused to be horizontal. Further, because the rods 53 and 54 are attached to the first and second panels 34 and 35 respectively, the first and second panels are thereby kept horizontal. The third and fourth panels 36 and 37 are kept horizontal by means of the springs (not shown) referred to above. It may also be desirable to use a spring between the first and second panels 34 and 35 in order to help the board 31a to stay flat.

The folding board 31b is at the point along the loop where the board has been caused to bend along its first fold line 38. This has been achieved because at this point, the tracks 56 and 58 are lower and closer together, whereby the rods 53 and 54 have been bent down. As a result, the first and second panels are bent down. This is the preferred direction for the first and second panels 34 and 35 to be bent, i.e. bent so the sheet contacting surface of the board is on the outside of the bend.

The folding board 31c is at the point along the loop where the third and fourth panels 36 and 37 have been bent up. This is the preferred direction for the third and fourth panels to be bent, i.e., toward the sheet contacting surface of the first and second panels. This has been achieved by means of a first stationary cam 62 and a second cam not shown. These cams are positioned so that the underside of the third and fourth panels is brought into contact with the cam as the board is moved along the chain. As the board continues to move, the third and fourth panels are pushed up and back. Preferably, the contacting surface on the cams is coated with a wear-resistant material such as teflon.

The folding board 31d has moved past the cams 62. As can be seen, the third and fourth panels have returned to being coplanar with the first and second panels respectively by means of the springs described above. Also, the board 31d has begun to point downward as the chain 32 is rounding the corner. The dashed line 91 represents the remainder of the path of the chain 32 while the dashed lines 92 and 93 represent the remainder of the path of the tracks 56 and 58 respectively.

Figure 6:
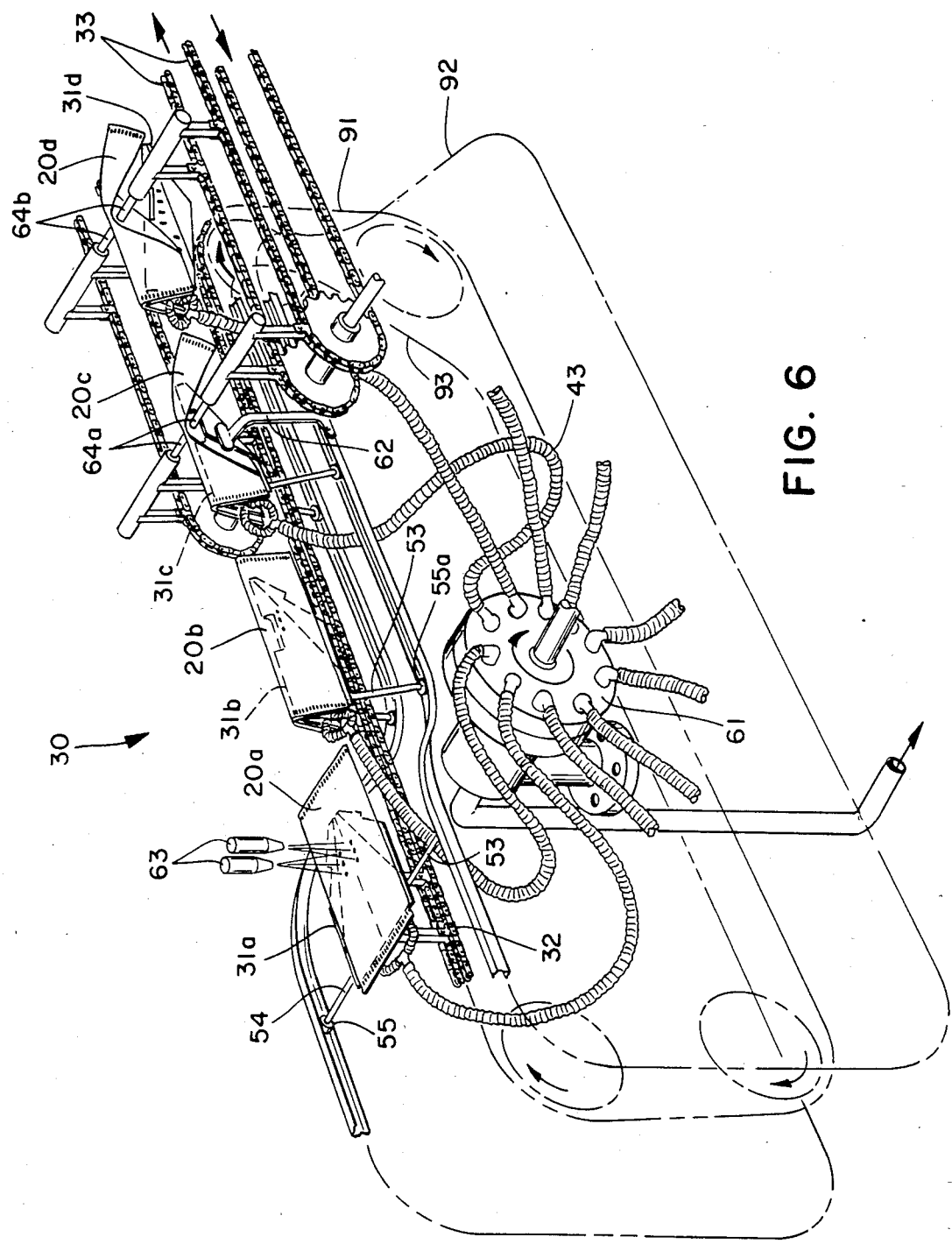
FIG. 6 is the same perspective view as FIG. 5 with the addition of flexible sheets on the folding boards, adhesive applicators, and means for removing the folded sheets from the folding boards.
Figure 7:
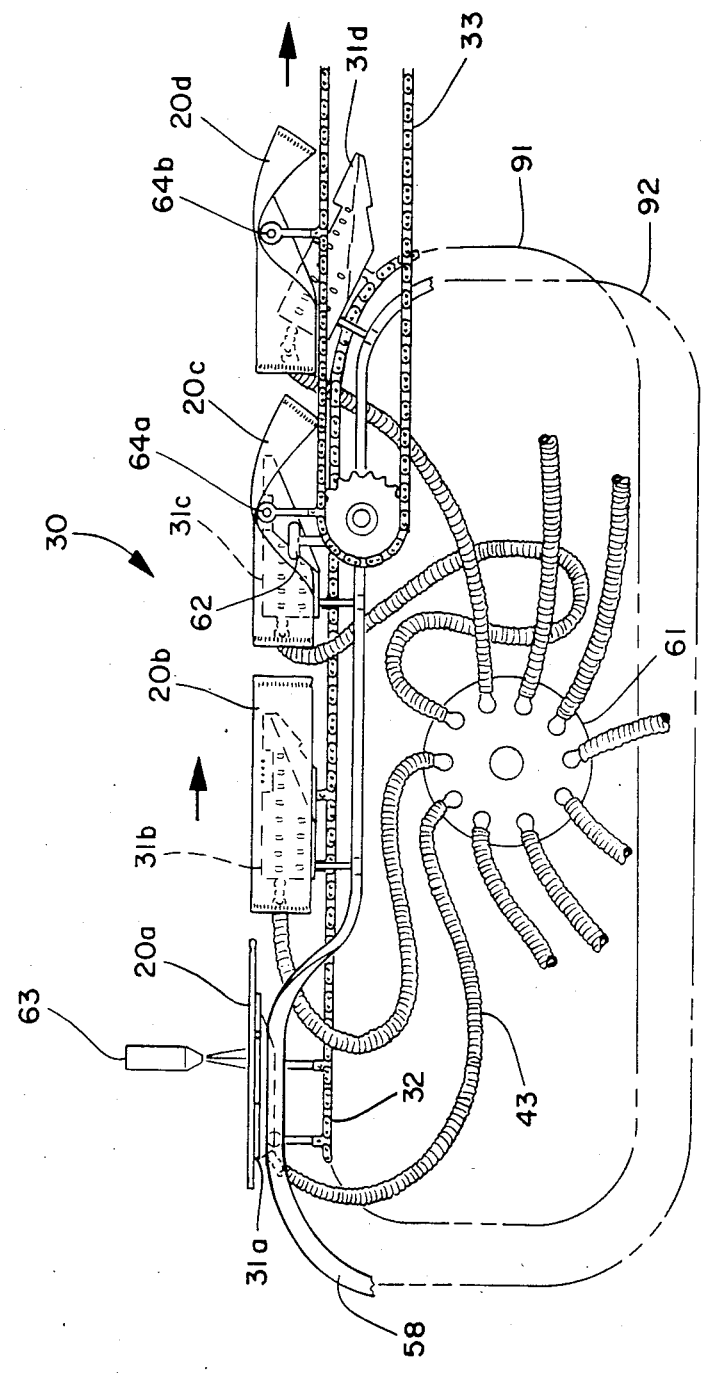
FIG. 7 is a side elevation of the apparatus shown in FIG. 6.

In FIGS. 6 and 7, the same apparatus 30 is illustrated with flexible sheets of material 20a–20d at various stages of folding on the folding boards 31a–31d.

The sheet 20a is retained on folding board 31a by means of the vacuum ports described in connection with FIG. 4. The sheet is put on the board so that the inner surface of the sheet, i.e. as worn, is facing down and thereby contacting the folding board. At this point an adhesive is applied to the sheet 20a by means of a glue gun 63. The adhesive is applied to the sheet 20a at a point which will help the sheet maintain the folds which are effected by the third and fourth panels. As can be seen, the front portion of the sheet 20 extends beyond the leading edge of the folding board 31a. This is important in forming the cup in the final garment.

The sheet 20b which is retained on the folding board 31b has now had a first fold formed in it, which first fold is centrally and longitudinally located in the sheet. This fold has been accomplished by the bending of the board 31b along its first fold line. Naturally, the sharpness of the fold thus created will depend on the material and thickness of the sheet. In the preferred embodiment, the sheet is about ¼" thick and the material is relatively flexible. Thus, this first fold is not very sharp or distinct.

The sheet 20c which is retained on the board 31c has now had a second and third fold formed in it, which folds originate at a common base point on the first, fold. These second and third folds extend between this common base point out to the sides of the sheet 20c. Preferably, the angle between the second and first fold is the same as the angle between the third and first fold. As can been seen, when these second and third folds are effected in the sheet 20c, the front part of the sheet is necessarily pushed downward. That is, the front part of the sheet is formed into a particular shape even though it is not attached to the folding board. This result is advantageous as it creates the cup and upwardly extending front portion in the final garment. Also it is because this downward movement of the front part of the sheet is desirable that it is important for the front part of the sheet to extend beyond the leading edge of the folding board.

Likewise, at this point, a pair of mechanical pincers 64a have closed on the sheet 20c. In particular, the pincers have pinched the top central part of the sheet 20c. One purpose of these pincers is to pick the sheet up so it can be removed from the folding board and moved to the next stage of assembly and/or packaging. In addition, the pincers help retain the folds in the sheet while the adhesive is drying. Preferably, the pincers are mounted in an endless loop on chains 33 which are moving at the same linear speed as the chain 32.

The sheet 20d is at the point of being removed from the board 31d. This is accomplished by virtue of the fact that the pincers 64b are moving in a straight line and the board 31d is starting to move down as the chain 32 is moving around the corner. Also, at or just before this point, the vacuum to the ports has been interrupted so the sheet is more easily removed.

Although in the preferred embodiment described above the folding apparatus included a plurality of folding boards, it may be desirable to construct an apparatus with a single folding board. Likewise, although the preferred apparatus moves the folding boards in an endless loop, it may also be desirable to construct an apparatus where the folding boards remain stationary and other means are provided for bringing the sheets of flexible material to and removing the sheets from the folding boards. In addition, although the preferred embodiment uses a system of cams, including rollers and tracks, to cause the bending of the folding boards, it may be desirable in alternative embodiments to utilize hydraulic or electrical means. Further, although it is preferable to use vacuum ports on the folding board to releasably retain the sheet on the board, other means such as mechanical grippers are available. Certainly, these and other modifications which will be apparent to one skilled in the art are considered within the scope of the present invention. The above description is therefore to be considered exemplary and explanatory rather than limiting, while the scope of the invention is to be determined by the following claims.

What is claimed is:

1. An apparatus for folding sheets of flexible material, the apparatus comprising:
   a plurality of folding boards each comprising means for folding the sheet, each folding board having a leading edge, a trailing edge and side edges, and further having a surface for contacting the sheet comprising four panels connected by three hinges, the first hinge being positioned and adapted for the folding board to bend between the first and second panel along a centrally located first fold line extending from the leading edge to the trailing edge, the second hinge being positioned and adapted for the folding board to bend between the first and third panels along a second fold line extending between the leading edge and one of the side edges, and the third hinge being positioned and adapted for the folding board to bend between the second and fourth panels along a third fold line extending between the leading edge and another of the side edges;

means connected to said folding boards for moving the plurality of folding boards in an endless loop, said endless loop having a straight line portion, thereby continually bringing each folding board into contact with a source of flexible sheets;

means contacting said folding boards for releasably retaining a flexible sheet on the folding boards during folding;

means to contact each folding board for bending each folding board along said first, second and third fold lines while said folding board is moving in said straight line portion of said endless loop;

means to apply adhesive to the flexible sheet retained on said folding board prior to folding for maintaining said sheet in its folded condition and clamping means are provided to hold the folded sheet in the adhesive area and to remove it from said folding board said clamping means moving in a straight line during said clamping.

2. The apparatus of claim 1 wherein the means for releasably retaining the flexible sheet comprises vacuum port means positioned on the folding boards and communicating with a vacuum source.

3. The apparatus of claim 1 wherein the means for bending the folding boards comprises a system of cams whereby movement of the folding boards in the endless loop causes the folding boards to bend along the first, second, and third fold lines.

4. The apparatus of claim 3 wherein the cam system comprises a pair of stationary cams which contact the third and fourth panels thereby causing the third and fourth panels to bend toward the first and second panels along the second and third fold lines respectively.

5. The apparatus of claim 3 wherein the cam system comprises a first and second rod means each having one end attached to the first and second panels respectively and an other end which moves within a first and second groove respectively, each groove being positioned and configured so as to cause the first and second panels to alternatively be substantially coplanar and bent toward each other along the first fold line.

6. The apparatus of claim 5 wherein the cam system further comprises a pair of stationary cams which contact the third and fourth panels thereby causing the third and fourth panels to bend toward the first and second panels along the second and third fold lines respectively.

7. The apparatus of claim 5 further comprising a first and second roller which are attached to the other end of the first and second rod means respectively, which rollers are adapted to roll in the first and second groove respectively.

8. A method of folding a sheet of flexible material, the method comprising:

providing a folding board for folding the sheet, the folding board having a leading edge, a trailing edge, and side edges, and further having a surface for contacting the sheet comprising four panels connected by three hinges, the first hinge being positioned and adapted for the folding board to bend between the first and second panel along a centrally located first fold line extending from the leading edge to the trailing edge, the second hinge being positioned and adapted for the folding board to bend between the first and third panels along a second fold line extending between the leading edge and one of the side edges, and the third hinge being positioned and adapted for the folding board to bend between the second and fourth panels along a third fold line extending between the leading edge and another of the side edges;

placing the sheet of flexible material on the surface of the folding board such that the front part of said sheet extends beyond the leading edge of the folding board;

causing the folding board to bend along the first fold line, thereby forming a first fold which is centrally and longitudinally located in the sheet;

causing the folding board to bend along the second and third fold line, thereby forming a second and third fold which both originate at a common base point on the first fold and which both extend from said common base point at an angle to the first fold to a respective side edge of the sheet thereby forcing said front part of said sheet downward creating a cup and an upwardly extending front portion in the garment formed from said sheet; and removing the garment from the surface of the folding board.

9. A method of folding a sheet of flexible material having length and width, the method comprising:

providing a plurality of folding boards for folding the sheet, each folding board having a leading edge, a trailing edge, and side edges, and further having a surface for contacting the sheet comprising four panels connected by three hinges, the first hinge being positioned and adapted for the folding board to bend between the first and second panel along a centrally located first fold line extending from the leading edge to the trailing edge, the second hinge being positioned and adapted for the folding board to bend between the first and third panels along a second fold line extending between the leading edge and one of the side edges, and the third hinge being positioned and adapted for the folding board to bend between the second and fourth panels along a third fold line extending between the leading edge and another of the side edges;

placing a sheet of flexible material on the surface of each of the folding boards;

applying adhesive to each of said sheets prior to folding to maintain said sheet in its folded condition, causing the folding boards to bend along the second and third fold lines, thereby forming a second and third fold which both originate at a common base point on the first fold and which both extend from said common base point at an angle to the first fold to a respective side edge of each sheet;

moving said boards in a straight line during folding of each of said sheets; and holding the folded sheet by clamps at the adhesive areas during removal of said sheets from the surface of the folding boards in a straight line movement of said clamps.

10. The method of claim 9 further comprising causing said folding boards to bend along the first fold line in one direction, and causing the folding boards to bend along the second and third fold lines in an opposite direction.

11. The method of claim 9 wherein the angle between the second and first fold is the same as the angle between the third and first fold.

12. The method of claim 9 further comprising causing said folding boards to move in an endless loop whereby said folding boards are continually brought into contact with a source of sheets of flexible material.

13. The method of claim 9 wherein said folding boards further comprise vacuum ports and wherein said sheet is caused to be releasably retained on the surface of the folding board during the folding of the sheet.

* * * * *